(12) United States Patent
Olalde Rangel

(10) Patent No.: US 7,498,048 B2
(45) Date of Patent: Mar. 3, 2009

(54) RENAL PHYTO-NUTRACEUTICAL COMPOSITION

(75) Inventor: Jose Angel Olalde Rangel, Clearwater, FL (US)

(73) Assignee: Jose Angel Olalde Rangel, Clearwater, FL (US)

( * ) Notice: Subject to any disclaimer, the term of this patent is extended or adjusted under 35 U.S.C. 154(b) by 0 days.

(21) Appl. No.: 11/420,520

(22) Filed: Nov. 16, 2006

(65) Prior Publication Data

US 2008/0118584 A1     May 22, 2008

(51) Int. Cl.
*A61J 36/00*    (2006.01)
*A61K 36/16*    (2006.01)
*A61K 36/537*    (2006.01)

(52) U.S. Cl. .................. 424/725; 424/195.15; 424/752; 424/746; 424/732

(58) Field of Classification Search ........................ None
See application file for complete search history.

(56) References Cited

U.S. PATENT DOCUMENTS 5,744,187 A * 4/1998 Gaynor ....................... 426/599

6,551,627 B1 * 4/2003 Yoon et al. .................. 424/725

OTHER PUBLICATIONS

HIV/AIDS Monitoring; Improved Viral Load Test Approved by FDA; Blood Weekly; Atlanta; Sep. 2002 pp. 1-2.*
Animal Models (HBV0; Trimera Disease Model Developed for Hepatitis B; Cancerweekly Plus; Atlanta; Feb. 1999 pp. 1-2.*
Davis, G. Treatment of Chronic Hepatitis C; British Medical Journal; Nov. 2001 pp. 1-3.*
Mylonakis et al. Plasma Viral Load Testing in the Management of HIV Infection; American Family Physician; Feb. 2001 pp. 1-7.*
Phillipson, J. New Drugs From Nature—it Could Be YEW; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*

* cited by examiner

*Primary Examiner*—Patricia Leith

(57) ABSTRACT

A Phytoceutical composition for the prevention and treatment of renal disorders is provided. A specific combination of extracts of plants is taught, as well as principles for varying the formulations based on categorizing plants into one of three groups, Energy, Bio-Intelligence, and Organization and selecting several plants from each group. Such combinations have effects, with minimal side effects.

1 Claim, 1 Drawing Sheet

Figure 1: Classification of phytomedicines and nutraceutical according to Energy, Bio-Intelligence and Organization.
Note: This figure contains no new matter.
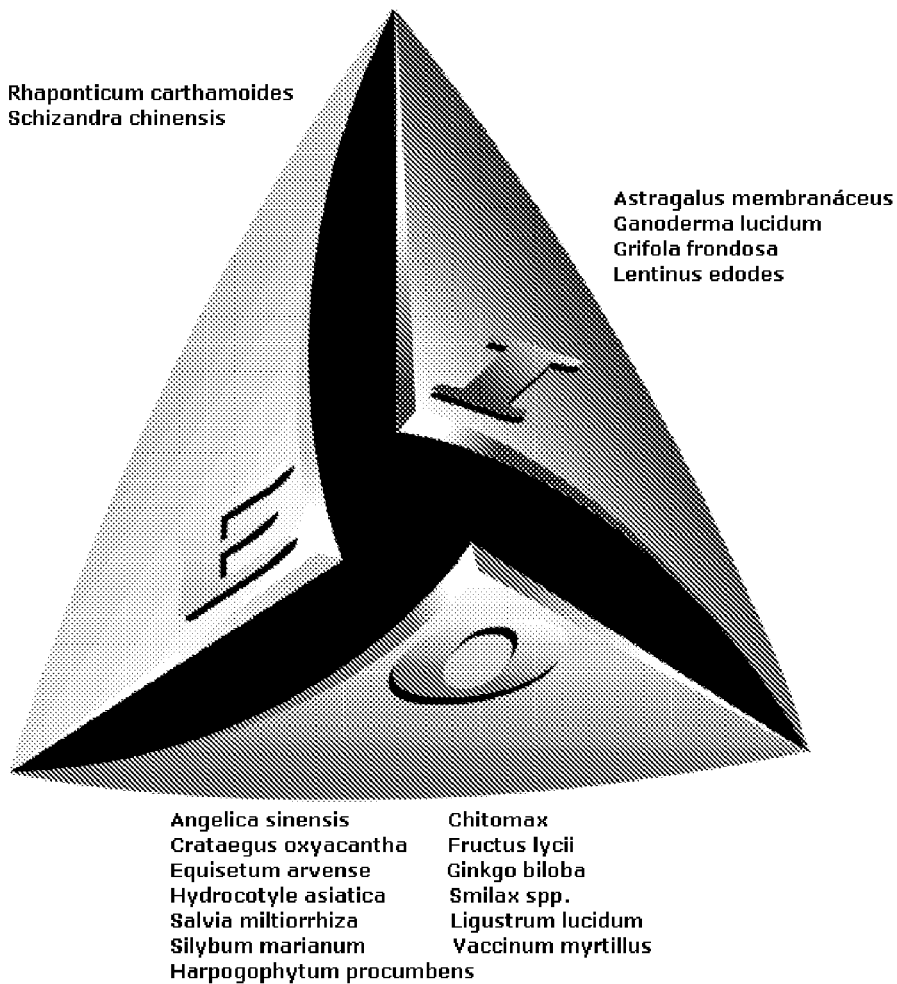

RENAL PHYTO-NUTRACEUTICAL COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat renal disease. The formulation is a particular combination of plants that have synergistic effect in combination. Principles for selecting beneficial formulations are provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process. As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines.

This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatment; however this can be marred by severe side effects. On the other hand, despite the excellent medicinal qualities of many plants, they are individually insufficient to take chronic degenerative diseases into remission. However, there is mounting evidence which demonstrates that medical plants contain synergistic efficacy and/or side-effect neutralizing combinations (Gilani and Rahman, 2005). Thus, what are needed in the art are better treatment regimes with improved patient tolerance, while providing sufficient efficacy. Thus, what are needed in the art are better treatment regimes with improved patient tolerance, while providing sufficient efficacy.

SUMMARY OF THE INVENTION

A number of known beneficial plants were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each category. Thus, one embodiment of the invention provides a method of selecting additional disease treating formulations according to these principles. An example of a formulation prepared this way is provided and additional formulations are being prepared and tested.

Another embodiment of the invention provides an effective, natural composition for treating chronic renal diseases. The composition can be used alone, or can be combined with simultaneous use of one or more pharmaceutical compositions. It can be used for the treatment of acute renal failure, diabetic nephropathy, nephritis, proliferative and non-proliferative glomerular diseases, renovascular hypertension, and other chronic nephropathies.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

EXAMPLE 1

Plant Characteristics—Renal Disorders

Energy Supplying Phytoceuticals

*Rhaponticum carthamoides* (*Leuzea*, or Maral Root) contains a mixture of compounds called 'levseins'. Levseins represents a complex of more than 10 ecdysterones including 20-beta-ecdysterone, makisterone C, 24-dehydromakisterone A, carthamosterone, polypodyne B and ajugasterone C. Researchers extracted and purified various ecdysteroids from *Rhaponticum* and found that the ecdysteroids increased the muscle mass in a dose-dependent manner, with the rate of increase proportional to the ecdysteroids content. In women with Chronic Renal Failure (CRF), low levels of estrogens are observed whereas in men a low level of testosterone is present. Ecdysterone behaves as an anabolic steroid mimicking the effects of these hormones. On the other hand, the severe and terminals cases of CRF are associated with anemia due to the decrease in renal production of erythropoietin.

The active principles of *Leuzea* offer erythropoiesis stimulating properties, which contribute to improve anemia. Incorporation of this phytomedicine in a composition provides at least 10 active principles in a single therapeutic.

*Schizandra chinensis* (also known as Wuweizi and Wurenchum) The major active principles of *Schizandra* are lignans called schizandrins. These substances have known nephro-protective; and hepato-protective properties. It maintains the integrity of hepatocyte cellular membranes; increases the levels of ascorbic acid; inhibits NADPH oxidation; inhibits lipid peroxidation at the hepatic microsomal level as well as formation of malondialdehyde; diminishes production of carbon monoxide; has an inductor effect in the enzymatic anti-toxic microsomal hepatic cytochrome P-450; increases biliary flow and the excretion of toxic substances; promotes recovery of hepatic functions; increases ornithine decarboxylase activity as well as the mitotic index, facilitates DNA and proteins synthesis; increases levels of glutathione and glutathione reductase, improving the regeneration capacity of the glutathione. *Schisandra chinensis'* different active principles increase energy levels by activating enzymes which participate in the production of ATP whose subsequent hydrolysis generates energy which is particularly significant in patients who suffer Chronic Renal Failure (CRF). This plant provides at least 81 active principles in a single therapeutic.

Bio-Intelligence Modulators

*Astragalus membranaceus* (Huang-Qi) This plant contains three main types of active principles. Isoflavones, which act as anti-oxidants; astragalans which act as immune-stimulants and anti-inflammatory by stimulating the phagocytic activity of macrophages, of the cytotoxic response of T and NK lymphocytes and of the production and activity of interferon; and astragalans which act as modulators of the hypothalamus-hypofisis-adrenal axis response. Cellular and humoral responses are altered in patients with CRF. The immune stimulating polysaccharides (astragalans) improve cellular and humoral non-specific immunity mechanisms. This is of great importance in patients at risk of infections, due to dialysis or immunosuppressant medication. Progress has been reported in the study of *Astragalus* therapeutic mechanism in the treatment of nephropathy. This plant provides at least 38 active principles in a single therapeutic.

*Ganoderma lucidum* (Reishi) *Ganoderma*'s main active principles are beta glucans and Proteoglucans. *Ganoderma* extract may protect the kidney from superoxide induced renal damages, due to the antioxidative effect on kidney lipid peroxidation; diminishing malonic dialdehyde levels, because of its prominent superoxide scavenging effect. Also, Glomerular endothelial dysfunction is believed to be responsible for the proteinuria and nephronal damage, namely tubule-interstitial fibrosis and glomerulosclerosis, observed in severe nephrosis such as focal segmental glomerulosclerosis. A successful suppression of proteinuria is accomplished by using *Ganoderma lucidum*. The beneficial effect of *Ganoderma lucidum* appears to be multi-factorial, including the modulation of immune-circulatory balance, anti-lipid, vasodilator, antiplatelet and improved hemo-rheology. This helps neutralize oxidative stress and suppress the toxic effect to the glomerular endothelial function. *Ganoderma lucidum* suppresses endothelial cell citotoxicity and proteinuria in persistent proteinuric focal segmental glomerulosclerosis. Other study results suggest that *Ganoderma* significantly reduces oxidative damages and apoptosis in human Proximal Tubular Epithelial Cells (PTEC) induced by Human Serum Albumin (HSA). The differential reductions of IL-8 or sICAM-1, released from HSA-activated PTEC by different components of the *Ganoderma*, could play different roles and operate different mechanisms in preventing HSA-induced PTEC damage. This mushroom incorporates at least 32 active principles in one therapeutic.

*Grifola frondosa* (Maitake, Dancing mushroom, Hongo bailarin; *G. sordulenta, Polyporus umbellatus y Meripilus giganteus*) Its active principles are chemically related to the β-D-glucan structure (that is d-glucose with other monosaccharides) or to protein linked β-D-glucans (called peptic-polysaccharides or Proteoglucans). These active principles modulate the human's Immune Intelligence, due to the increase in the production of humoral immune response mediators, such as: interleukin (10, 12), TNF-α, Nitric Oxide and Interferon-gamma; inducing macrophage activation. Also, they improve the NK lymphocytes' activity. D-Fraction, a polysaccharide extracted from the edible Maitake mushroom (*Grifola frondosa*), activate immune-competent cells, thereby eliciting antitumoral activity. A recent study indicates that it also enhances both the innate and adaptive arms of the immune response. Therefore, its administration may enhance host defense against foreign pathogens and protect individuals from infectious diseases (common in patients with nephropathies). This mushroom incorporates at least 6 active principles in one therapeutic.

*Lentinus edodes* (Shiitake): *Lentinus edodes* (LE) active principles are mainly present as glucans with different types of glycoside linkages such as (1—>3), (1—>6)-beta-glucans and (1—>3)-alpha-glucans, and as true hetero-glycans, act as immune modulators due to the increase in the concentration of humoral mediators of the immune response, such as: gamma interferon, interleukins 2 and 6, nitric oxide production, catalase activity in macrophages and lymphocytes T. Also, they activate the citotoxic activity of NK cells and macrophages. Results of in vivo studies demonstrated that the antitumoral activity of the polysaccharide L-II on transplanted sarcoma 180 was mediated by immunomodulation in inducing T-cells and macrophage-dependent immune system responses. Other studies suggest that LE may induce Th immune responses. Finally, another study points out that the water-soluble rich fraction of LE, had antiviral and immunopotentiating activities.

Organization Enhancers

*Angelica sinensis* (Dong quai or *Angelica*, also *Angelica archangelia, Angelica pubescens* and *Angelica sylvestris* Can qui, Angelica china, dangdanggui, dang gui, dong quai, duong qui, handanggui, hashyshat almalak, kara toki, langdu danggui, min-gui, tang-kuei, and tân q́ ui) Contains terpenes (terpenes, mainly β-phellandrene, with β-bisabolene, β-caryophyllene, β-phellandrene, α- and β-pinene, limonene, linalool, borneol, acetaldehyde, menthadienes and nitromenthadienes), macrocyclic lactones (including tridecanolide, 12-methyl tridecanolide, pentadecanolide), phthalates (such as hexamethylphthalate), coumarins (especially furocoumarin glycosides such as marmesin and apterin), angelicin and byakangelicin derivatives (osthol, umbelliferone, psoralen, bergapten, imperatoren, xanthotoxol, xanthotoxin, oxypeucedanin and more), as well as various sugars, plant acids, flavonoids, and sterols. It also, contains alkyl phthalides (Ligustilide); terpenes, phenylpropanoids (ferulic acid) and benzenoids. These substances stimulate the immune system's actions, through diverse lymphokines and have an anti-inflammatory effect by inhibiting 5-lipoxygenase and elastase, as well as selectively inhibiting 12-(S)—HHTrE production, a marker of cyclo-oxygenase activity.

*Angelica* has been reported to be clinically effective for erythropoietin (EPO)-resistant anemia in chronic renal failure. These components have vasodilator activity, increase coronary flow and are antithrombotic. The incorporation of this phytomedicine into compositions provides at least 70 active principles in a single therapeutic.

*Crataegus oxyacantha* (Hawthorn, see also *C. monogyna*) contains mainly flavonoids (such as flavonoglycosyls, hyperoside, rutin, flavonol, kaempferol, and quercetin) and oligomeric procyanadins (1-epicatechol), which relax arterial expansion to decrease peripheral vascular resistance. Also contains amines (phenyletylamine, tyramine, O-methoxyphenethylamine), flavone (apigenin, luteolin) derivatives, vitexin glycosides, tannins, saponins, and cyanogenetic glycosides. Its active principles—tannins—decrease blood levels of urea nitrogen, creatinine and urinary levels of protein and glucose. They increase glomerular filtration rate and renal blood flow. Its nephro-protective action is partly due to its antioxidant effect. Tannins produce a reduction in methylguanidine, a substance that accumulates in the blood when there is renal failure. Tannins decrease the progression of renal failure by lessening mesangial proliferation and glomerular sclerotic lesions. It also inhibits Thromboxane (TXA2) biosynthesis which in turn lessens mesangial proliferation and pro-coagulant activity within the mesangial cell. High-performance liquid chromatography has been used to analyse qualitative and quantitative compounds in *Crataegus* such as [3H]-(-) epicatequina 3-O-gallate (ECG). This compound (ECG) is an active component of Onpi-to a chronic renal failure herbal medicine. The incorporation of this phytomedicine into a composition provides at least 52 active principles in a single therapeutic plant.

Chitomax (Chitosan and Vitamin C) Chitosan is a linear polysaccharide composed of randomly distributed β-(1-4)-linked D-glucosamine (deacetylated unit) and N-acetyl-D-glucosamine (acetylated unit). Chitosan is produced from chitin also, which is the structural element in the exoskeleton of crustaceans (crabs, shrimp, etc.). Its major active principle are long amino-polysaccharide molecules (N-acetyl-D-glucosamine), which contain groups of positively charged free amino acids allowing chemical bonding with negatively charged fatty and biliary acids. Chitosan also inhibits some pancreatic enzymes such as lipase and amylase; associated with acute pancreatitis. Chitosan's action is boosted when combined with other compounds such as vitamin C. Scientific evidence points to its lipid removal capabilities, 5 to 10 times greater than other fibers such as cellulose, chitin or agar. It also diminishes uric acid levels and acts as an anti-acid, improving Ca absorption. It significantly reduces total seric cholesterol; lipoprotein, uremic toxins, urea and blood creatinine levels; increasing hemoglobin levels in patients with hemodialysis treatment due to Chronic Renal Failure (CRF). Scientific studies have found Chitosan to be a natural-based nontoxic, biocompatible, and biodegradable polymer with anti-microbial activity. Chitosan and its derivatives could accelerate wound healing by enhancing the functions of inflammatory cells and repairing cells. Recent studies further indicated that chitosan and its derivatives also are novel scaffold materials for tissue engineering and are-promising non-viral vectors for gene delivery.

*Equisetum arvense*(Horse tail) This plant contains abundant mineral salts particularly silicic acids and silicates. It also contains phytosterols, phenolic acids, flavonoids (mainly quercetin glycosides and apigenine) and saponins (equisetonin). These active principles block the liberation of arachidonic acid, which diminishes inflammation and confer it diuretic properties, of importance in oliguria, renal failure, hyperuricaemia, arterial hypertension or edemas.

*Fructus lycii*(*Lycium barbarum* fruits, wolfberry, Gouqi) Contains polysaccharides and carotenoids which improve renal functions; accelerates the depuration—clearance—of degradation products such as blood urea nitrogen. They improve the adaptation to exercise resistance and reduce fatigue. Increase hepatic and muscle glycogen reserves. *Fructus lycii* can ameliorate insulin resistance, and the mechanism may be involved in increasing cell-surface level of GLUT4, improving GLUT4 trafficking and intracellular insulin signaling. The modulation of a polysaccharide-protein complex from Lycium barbarum (LBP3p) on the immune system has a highly significant effect on tumor weight and improves the immune system. Adding LBP to cancer treatment led to more marked increase in NK and LAK cell activity than LAK/IL-2 without LBP. The results indicate that LBP can be used as an adjuvant in the biotherapy of cancer. In another study LBP demonstrated a strong anti-oxidative activity inhibiting lipid peroxidation, capturing superoxide anions and preventing malondialdehyde formation, diminishing DNA damage caused by oxidative stress. The incorporation of this phytomedicine into a composition provides at least 35 active principles in a single therapeutic.

*Ginkgo biloba* (*Ginkgo*) contains ginkgolides, bilobalides, bioflavones and flavone glycosides. Flavone glycosides include quercetin, 3-methylquercetin and kaempferol. Quercetin, myrcetin and the rest of the flavonoid fraction of the extract have antioxidant and free radical scavenger effects. The flavonoids diminish infiltration by neutrophils and increase blood flow. Their antioxidant properties and membrane stabilizing activity increase the tolerance to hypoxia. They improve cellular metabolism and protect against the damage caused by ischemia. Ginkgolide B is a powerful PAF inhibitor, which bonds to membrana receptors and is a antagonist of platelet agregation. A *Ginkgo* extract demonstrated capabilities to reduce seric hiperlipidemia. It also has anti-inflammatory properties by reducing vascular permeability and has vasodilator effects by inhibiting the liberation of thromboxane A2 and protaglandines. Controlled double blind clinical studies conclusively demonstrate the effectiveness of *Gingko biloba* in treating arterial insufficiency. *Gingko* is effective in treating incipient nephropathy through the reduction of the reduction of the albumina excretioin rate in urine, regulating lipids in the blood, improving renal function and hemeorhology. IN a recent study the administration of gingko during 3 months significantly reduced malonaldehide levels in the erythrocyte membranes, diminished the fibrinogen levels, promoted the deformatoion of erythrocytes and improved the viscocity and visco-elasticety of the blood, which facilitated blood perfusion. *Gingko* improved the kidneys' function, stimulating the anti-oxidative defenses, diminishing the lipidic peroxidation rate, which reduces renal damage. Increases the renal blood flow and improves the renal excretion function. The incorporation of this phytomedicine into a composition provides at least 59 active principles in a single therapeutic.

*Harpagophytum procumbens* (Devil's Claw) The endothelial damage to the glomerular capillary produces the liberation of the Platelet Aggregation Factor (PAF) and the Hageman factor leading to formation of platelet thrombus. Activated platelets produce Thromboxane A2 (TXA2) and additional PAF, which increase glomerular sclerosis. The active principles of *Harpagophytum procumbens*—harpagosides, harpagine, procumbides, procumbosides, beta-sitosterol and stigmasterol diminish TXA2 by inhibition of thromboxane synthetase. They also diminish the inflammation process, inhibiting Cycloxigenase and Nitric Oxide Synthase, which leads to a reduction in the synthesis of the pro-inflammatory substances prostaglandin E2 (PGE2) and nitric oxide. Incorporation of this phytomedicine in a composition provides at least 34 active principles in a single therapeutic.

*Hydrocotile asiatica* (Gotu Kola, Bramhi, Pennywort, Marsh Penny) contain terpenoids (triterpenes, asiaticoside, brahmoside and brahminosidea, aglycones-saponin glycosides, asiaticentoic acid, centellic acid, centoic acid and madecassic acid) sesquiterpenes (caryophyllene, trans-B-farnesene), volatile oils (Germacrene D), alkaloids (hydrocotylin), flavones (Quercetin, kaempferol, sesquiterpenes, stigmasterol, and sitosterol), and vallerine, fatty acids, resin, and tannins.

Quercetin, an anti-oxidant, has been demonstrated to attenuate diabetic nephropathy. Fitosterols reduce cholesterol levels; have immune-modulating and anti-inflammmatory properties. Incorporation of this phytomedicine in a composition provides at least 59 active principles in a single therapeutic.

*Ligustrum lucidum* (Glossy privet, Chinese Privet, Nepal Privet, Nu Chen, Nu Chen P'I Chiu, Nu-zhen-zi, To-Nezumi-Moti) Its main active principles are ligustalosides, ligustrosidic acid, oleuropein, alpha-mannitol, oleanolic and oceanic acids and secoiridoid glucosides. These substances improve diabetic nephropathy because they suppress the protein glycosylation and reduce the cytokine expression at the renal level; they also exhibit strong antioxidant effect against hemolysis of red blood cells induced by free radicals. Data suggest that these phytochemicals may exert antitumoral effects via augmentation of phagocyte and LAK cell activities. Incorporation of this phytomedicine in a composition provides at least 18 active principles in a single therapeutic.

*Salvia miltiorrhiza* (Chinese Sage, Huang Ken, Radix Salvia, Red Sage, Salvia Root, Dan Shen) The main active principles are cryptotanshinone, hydroxytanshinone, isocryptotanshinone, isotanshinone (I, II and III), methyl-tanshinonate, methyl-tanshinone, miltirone, salvianolic-acid-a, salviol, tanshinone (I, II and IIa); Tanshinolactone, danshenspiroketallactone, tanshinone-IIIb, tanshinonic-acid and lithospermic acid B. In vivo study demonstrated that *Salvia miltiorrhiza* can protect from diabetic nephropathy by suppressing the over-expressions of TGF-beta1, CTGF, PAI-1 and FN in renal cortex. In yet another in vivo study, a formulation which included *Salvia* was used in chronic and acute renal insufficiency models, improving both serum creatinine and urea nitrogen in both models. A daily parenteral application of *Salvia* improves blood microcirculation and decrease the incidence of renal function recovery retardation. These effects are helpful in the recovery of renal function after renal transplantation. *Salvia* can alleviate the injury of free radicals in organism, so it is an ideal remedy for the treatment of Henoch-Schonlein purpura nephritis (HSPN). Conventional treatment supplemented with *Salvia* Injection could more effectively improve the levels of plasma ET and SIL-2R in treating Primary Nephritic Syndrome children, and hence alleviate the damage of renal tissue. Its administration with other herbal medicine during peritoneal dialysis has important significance in improving the defense function of peritoneal macrophages, reducing the incidence of peritonitis and enhancing the therapeutic effect of peritoneal dialysis. Incorporation of this phytomedicine in a composition provides at least 27 active principles in a single therapeutic.

*Silybum marianum* (Milk Thistle, Carduus marianus, Holy thistle, Marian thistle, and Mary thistle) The active principles of this plant are flavonolignans, including silibine, silicristine and silidianine and isosilibinin collectively known as sylimarin. This compound has the highest grade of nephro-protective, hepato-generating, and anti-inflammatory activity. The mechanisms which explain its therapeutic characteristics are diverse and include anti-oxidation, lipid anti-peroxidation, detoxification increase through a competitive inhibition with toxic substances, as well as protection against the depletion of glutathione. One of the mechanisms that can explain its properties is the increase in protein synthesis, obtained thanks to a significant boost in the formation of ribosomes, DNA synthesis and proteins at the hepatic level, because the active principles join a specific polymerase receptor, stimulating ribosome formation. Its anti-inflammatory effect is due to the stabilization of the mastocytes, the inhibition of neutrophils, a strong inhibition of leucotriene (LT) synthesis and formation of prostaglandins. Sylimarin inhibits intestinal beta-glucuronidase enzymes, thus improving glucoronization, which is an important step in hepatic detoxification. More corporal toxins are removed via glucoronization than through other detox pathways. In vitro experiments with kidney cells damaged by paracetamol, cisplatin, and vincristin demonstrated that administration of silibinin before or after the chemical-induced injury can lessen or avoid the nephrotoxic effects. The incorporation of this phytomedicine into a composition provides at least 57 active principles in a single therapeutic.

*Smilax* spp. (sarsaparilla, zarzaparrilla) Its main active principles are: phytosterols, Steroid Saponins, Phenolic acids, Flavonoids and minerals. These substances adhere to toxins inside the gastrointestinal tract, this way reducing their absorption by the circulatory stream. On the other hand it improves the hepatic and renal excretory functions, facilitating the removal of toxic substances and waste found in cells, blood vessels and lymphatic system. Also, phytosterols block prostaglandin synthetase action, explaining its anti-inflammatory action. Incorporation of this phytomedicine provides at least 35 active principles in a single therapeutic.

*Vaccinium myrtillus* (European blueberry or bilberry, closely related to American blueberry, cranberry, and huckleberry) *Vaccinium* contains anthocyanosides such as: cianadins, malvidins, petunidins and peonidins. Other ingredients include arbutin, asperuloside, astragalin, beta-amyrin, caffeic-acid, catechin, chlorogenic-acid, cyanadin-3-O-arabinoside, dihydroxycinnamic-acid, epicatechin, epigallocatechin, epimyrtine, ferulic-acid, gallic-acid, gallocatechin, hydroquinone, hyperoside, isoquercitrin, lutein, coumaric-acids, m-hydroxybenzoic-acid, monotropein, myrtillin, myrtillol, myrtine, neomyrtillin, protocatechuic-acid, quercetins, quinic-acid, resinic-acid, syringic-acid, ursolic-acid, and vanillic-acid. Evidence suggests that anthocyanosides may benefit the retina, as well as strengthen the walls of blood vessels, reduce inflammation, and stabilize collagen containing tissues. The anthocyanosides improve the activity of enzymes lactic dehydrogenase, glucose-6-phosphatase and phosphoglucomutase, each involved in processes of vascular damage. They reduce the arterial deposits and stimulate the production of vasodilators, like prostaglandin (PGI2), thus protecting the vascular wall. Anthocyanosides have strong antioxidant properties, as well. The incorporation of this phytomedicine provides at least 63 active principles in a single therapeutic.

EXAMPLE 2

Composition—Renal Disorders

A particularly preferred composition is shown in Table 1. Ratios reflect the concentration of active ingredient over the natural state, and the amounts provided are mg of extract.

Obviously, the amount should be increased where the strength is reduced, and vice versa.

A particularly preferred composition is shown in Table 1.

TABLE 1

Preferred Renal disorder Protocol

| Active Agent | Ratio | Amount (mg) |
| --- | --- | --- |
| Energy enhancers | | |
| Rhapontium carthamoides root extract | 6:1 | 6.00 |
| Schizandra chinensis fruit extract | 5:1 | 10.0 |
| Bio-Intelligence modulators | | |
| Astragalus membrenaceus root extract | 5:1 | 50.00 |
| Ganoderma lucidum | 5:1 | 24.00 |
| Grifola frondosa | 5:1 | 24.00 |
| Lentinus edodes | 5:1 | 24.00 |
| Organizational Improvers | | |
| Angelica sinensis root extract | 5:1 | 57.00 |
| Chitosan powder | 1:1 | 398.00 |
| Crataegus oxycantha berry extract | 5:1 | 40.00 |
| Equisetum arvense herb extract | 5:1 | 30.00 |
| Fructus lycii | 5:1 | 24.00 |
| Gingko bilova leaf extract | 50:1 | 17.00 |
| Harpagophytum procumbens tuber extract | 5:1 | 27.00 |
| Hydrocotile asiatica herb extract | 5:1 | 30.00 |
| Ligustrum lucidum | 5:1 | 24.00 |
| Salvia miltiorrhiza | 5:1 | 24.00 |
| Silybum marianum herb extract | 5:1 | 30.00 |
| Smilax regelii root extract | 5:1 | 27.00 |
| Vaccinum myrtillus fruit extract | 5:1 | 34.00 |
| Total | | 900 |

EXAMPLE 3

Tolerance Studies

A multicenter, retrospective study was made on 100 healthy volunteers with the intention of evaluating patient tolerance and side effects of the herbaria combination. A capsule containing 900 mg of the herbaria of Table 1 was administered to each participant three times per day for five days. During that period they were evaluated by a physician, who registered any finding or symptom reported by each subject. The average age of the participants was 37.4 years with a SD of 8.2 years. Gender was 55% female, 45% male. The average weight of the subjects was 70 kilos with a SD of 12.3 kilos. No undesirable effects were observed in 96% of the subjects. Four (4%) subjects reported minor undesirable effects.

The study showed that herbaria were well tolerated-only minor symptoms were reported by 4 of the 100 subjects. Results showed the non-toxicity of the herbaria, demonstrating that the formulation is safe. Similar results have been obtained for the PCOS and Psoriasis formulations.

EXAMPLE 4

Chronic Renal Failure Clinical Study Effectiveness and Tolerance

A retrospective, descriptive, multicenter, study based in the clinical records of all patients diagnosed with Chronic Renal Failure which attended Adaptogenic Medical Centers and Units in Venezuela, during a period that extends from April 2002 to July 2004. Data collected was: age, gender, and etiology, degree of CRF according to severity, patients' symptoms, Quality of Life parameters and treatment tolerance. Criterion for classification of severity was a time variation of the creatinine clearance, that is, the quantity of creatinine (milliliters) filtered per minute, according to table 2 below—which also includes gender and age per group.

TABLE 2

Patient classification according to CRF severity grading

| Severity | Creatinine clearance (ml/min) | N° of patients | % | Gender - Average age |
| --- | --- | --- | --- | --- |
| Slight | 30-70 | 19 | 16 | F: 8; M: 11-51 yrs. |
| Moderate | 15-30 | 47 | 38 | F: 21; M: 26-51 yrs. |
| Severe | 10-15 | 28 | 23 | F: 17; M: 11-51 yrs. |
| Terminal | <10 | 28 | 23 | F: 9; M: 19-57 yrs. |

Creatinine clearance values under 10 ml/min. were considered a criterion for dialysis requirement. Improvement in life quality was measured according to the Grogono-Woodgate Quality of Life index. All patients continued their treatment with synthetic pharmaceuticals in accordance with the base pathology.

Inclusion Criteria and Systemic therapeutic formulation Patients of any age or gender with a CRF diagnosis examined and controlled in our Adaptogenic Medical Centers or Units which followed the Systemic Treatment. Average age was 52.63 yrs old. Most frequent cause for CRF was arterial hypertension with 35.2%; Diabetes Mellitus was second with 25.4%. The rest of the population was associated with glomerular nephritis, kidney cysts and renal lithiasis.

Patients had to follow the product dosage indications i.e. received 10 capsules—900 mg, each—3 times a day, during six months.

Results: These are depicted in Table 3.

TABLE 3

Synopsis of CRF Study Results

| | Slight | | Moderate | | Severe | | Terminal | |
| --- | --- | --- | --- | --- | --- | --- | --- | --- |
| Evolution | Patients 19 | % | Patients 47 | % | Patients 28 | % | Patients 28 | % |
| Improvement | 0/19 | 0 | 16/47 | 34.04 | 19/28 | 67.85 | 17/28 | 60.71 |
| Deterioration detained | 14/19 | 73.68 | 22/47 | 46.8 | 7/28 | 25.0 | 11/28 | 39.28 |
| Deteriorated | 5/19 | 26.32 | 9/47 | 19.14 | 2/28 | 7.14 | 0/28 | 0 |
| QoL Improvement | 15/19 | 78.94 | 40/47 | 85.1 | 27/28 | 96.42 | 27/28 | 96.42 |

Conclusions Significant improvements were made in the Terminal and Severe (CRF) groups—60.7% and 67.85% of the treated patients, respectively. The change to a lower stage or degree of severity in 17/28 patients with Terminal CRF raises the possibility of suspending hemodialysis in those patients. Independently of the severity of CRF, in 54 out of the 122 patients the progression of the illness was stopped. Tests demonstrated the normalization of renal function in 4 patients. This proves nephro-protecting and nephro-regenerating capabilities of this therapeutic combination and establishes the possibility that a more prolonged use of this therapy may lead to the reestablishment of renal functions in a greater number of patients. This therapeutic formulation was highly effective in improving life quality in all stages of CRF. However, if in the slight and moderate cases of CRF the improvement in Quality of Life was a successful 78.9% and 85.1% respectively, the improvement in quality of life for severe and terminal groups was an outstanding 96.4% for both stages. Tolerance to treatment was exceptional. Only one patient presented slight gastric symptoms which did not prevent him from continuing his therapy. In conclusion: we consider that treatment with medicinal plants under the precepts of Systemic Medicine offers invaluable and unexpectedly superior clinical benefits as well as remarkable improvement in quality of life in patients suffering Chronic Renal Failure which do not always obtain satisfactory results with conventional therapeutic alternatives.

EXAMPLE 5

Principles for Selecting Synergistic Combinations

In order to explain the range of formulations encompassed by the invention, we have categorized beneficial plants into one of three groups, each of which should be present for synergistic effect. The classifications are: Energy, Bio-Intelligence and Organization. Plants classified under Energy are associated with ATP synthesis (such as the Krebs cycle, oxidative phosphorylation, beta-oxidation, etc.). Plants classified under Bio-Intelligence are those that regulate the neuroendocrine and immunological systems and cellular processes, thus controlling the interactions between the various systems in the body. Finally, plants classified under Organization are those that relate to the structure and function of specific organs. Combinations of plants from these three classification groups have synergistic effect because they address each necessary component of cellular and organic health—in effect they provide the triangle on which healing is fully supported. To illustrate this, FIG. 1 is provided.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated *Hydnocarpus wightiana*). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000 Feb. 15; 97(4):1433-7.

A further demonstration may be provided of synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Gohil, et al., mRNA Expression Profile of a Human Cancer Cell Line in Response to *Ginkgo Biloba* Extract: Induction of Antioxidant Response and the Golgi System, Free Radic Res. 2001 December; 33(6):831-849.

Finally there may be further presentation of gene expression results using whole-genome microarray analysis to demonstrate the formulation's capability to provide gene activation (upregulation or downregulation).

What is claimed is:

1. A phytoceutical composition, wherein said composition comprises: 6 mg of *Rhaponticum carthamoides* extract, 10 mg of *Schizandra chinensis* extract, 50 mg of *Astragalus membranaceus* extract, 24 mg of *Ganoderma lucidum* extract, 24 mg of *Grifola frondosa* extract, 24 mg of *Lentinus edodes* extract, 57 mg of *Angelica sinensis* extract, 398 mg of *Chitosan* extract, 40 mg of *Crataegus oxyacantha* extract, 30 mg of *Equisetum arvense* extract, 24 mg of *Fructus lycil* extract, 17 mg of *Ginkgo biloba* extract, 27 mg of *Harpagophytum procumbens* extract, 30 mg of *Hydrocotile asiatica* extract, 24 mg of *Ligustrum lucidum* extract, 24 mg of *Salvia Miltiorrhiza* extract, 30 mg of *Silybum marianum* extract, 27 mg of *Smilax regetii* extract, and 34 mg of *Vaccinium myrtillus* extract together with pharmaceutically acceptable excipients.

* * * * *